US012565521B2

(12) United States Patent　(10) Patent No.: US 12,565,521 B2
Choi et al.　(45) Date of Patent: Mar. 3, 2026

(54) SYSTEMS, KITS, AND METHODS FOR FORMING IN SITU SILK FIBROIN FIBERS AND/OR AEROSOLS

(71) Applicant: Trustees of Tufts College, Medford, MA (US)

(72) Inventors: Jaewon Choi, Cambridge, MA (US); Jugal Kishore Sahoo, Belmont, MA (US); Onur Hasturk, Medford, MA (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 301 days.

(21) Appl. No.: 18/501,326

(22) Filed: Nov. 3, 2023

(65) Prior Publication Data

US 2024/0401242 A1　Dec. 5, 2024

Related U.S. Application Data

(63) Continuation of application No. PCT/US2022/028323, filed on May 9, 2022.

(60) Provisional application No. 63/201,679, filed on May 7, 2021.

(51) Int. Cl.
| | |
|---|---|
| *C07K 14/435* | (2006.01) |
| *A61K 47/42* | (2017.01) |
| *B01F 23/40* | (2022.01) |
| *B01F 23/45* | (2022.01) |
| *B01F 23/80* | (2022.01) |
| *B01F 25/60* | (2022.01) |
| *B01F 101/22* | (2022.01) |
| *B05B 7/24* | (2006.01) |
| *B05B 15/20* | (2018.01) |
| *D01D 5/40* | (2006.01) |
| *D01F 1/10* | (2006.01) |
| *D01F 4/02* | (2006.01) |

(52) U.S. Cl.
CPC ........ *C07K 14/43586* (2013.01); *A61K 47/42* (2013.01); *B01F 23/405* (2022.01); *B01F 23/45* (2022.01); *B01F 23/48* (2022.01); *B01F 23/80* (2022.01); *B01F 25/60* (2022.01); *B05B 7/24* (2013.01); *B05B 15/20* (2018.02); *D01D 5/40* (2013.01); *D01F 1/10* (2013.01); *D01F 4/02* (2013.01); *B01F 2101/22* (2022.01);

*B01F 2215/0431* (2013.01); *B01F 2215/044* (2013.01); *D10B 2211/22* (2013.01); *D10B 2509/00* (2013.01)

(58) Field of Classification Search
CPC ..... C07K 14/43586; B05B 15/20; B05B 7/24; B01F 23/80; B01F 23/405; B01F 25/60; B01F 23/48; B01F 23/45; B01F 2101/22; B01F 2215/0431; B01F 2215/044; A61K 47/42; D01D 5/40; D01F 1/10; D01F 4/02; D10B 2221/22; D10B 2509/00
See application file for complete search history.

(56) References Cited

U.S. PATENT DOCUMENTS

| | | | | |
|---|---|---|---|---|
| 8,071,722 B2 * | 12/2011 | Kaplan | ............... | A61L 27/3604 |
| | | | | 530/353 |
| 2019/0186050 A1 | 6/2019 | Numata et al. | | |

FOREIGN PATENT DOCUMENTS

WO　　　2022236168 A1　11/2022

OTHER PUBLICATIONS

Mitropoulos , "Silk fibroin nanostructured materials for biomedical applications", UniversityProQuest Dissertations Publishing, Retrieved from the internet: <URL: https://www.proquest.com/dissertations-theses/silk-fibroin-nanostructured-materials-biomedical/docview/1690826392/se-2>, 2015, pp. 40-63.
PCT/US2022/028323 , "International Application Serial No. PCT/US2022/028323, International Search Report and Written Opinion mailed Aug. 30, 2022", Tufts University, 11 pages.

* cited by examiner

*Primary Examiner* — Shirley V Gembeh
(74) *Attorney, Agent, or Firm* — GTC Law Group PC & Affiliates

(57) ABSTRACT

Methods, spray devices, and kits for the in situ formation of silk fibroin fibers and/or aerosols are disclosed. Rapidly mixing a silk fibroin solution and a beta sheet initiation solution forms a mixed solution, which is rapidly expanded to form the silk fibroin fibers and/or aerosols. The beta sheet initiation solution includes a hygroscopic polymer having a molecular weight of between 7.5 kDa and 15.0 kDa. The rapid mixing and rapid expanding occur within one second of one another. Silk fibroin aerosols are formed when a molecular weight distribution of fragments in the silk fibroin solution is below an aerosol-fiber threshold. Silk fibroin fibers are formed when the molecular weight distribution is below the aerosol-fiber threshold.

25 Claims, 5 Drawing Sheets

Specification includes a Sequence Listing.

SYSTEMS, KITS, AND METHODS FOR FORMING IN SITU SILK FIBROIN FIBERS AND/OR AEROSOLS

CROSS-REFERENCE TO RELATED APPLICATIONS

This application is a bypass continuation of International Application Serial Number PCT/US2022/028323, filed May 9, 2022. International Application Serial Number PCT/US2022/028323 is related to and claims priority to U.S. Provisional Patent Application No. 63/201,679, filed May 7, 2021. Each of the foregoing patent applications is incorporated herein by reference in their entirety for all purposes.

STATEMENT REGARDING FEDERALLY FUNDED RESEARCH

This invention was made with government support under grant FA9550-20-1-0363 awarded by the United States Air Force. The government has certain rights in the invention.

SEQUENCE LISTING

A Sequence Listing accompanies this application and is submitted as an XML file of the sequence listing named "T002520 US2,095,0566_ST26.xml" which is 34 kbytes in size and was created on Feb. 9, 2024. The sequence listing is electronically submitted via Patent Center and is incorporated herein by reference in its entirety.

BACKGROUND

Spray techniques are useful forms for the rapid delivery of therapeutic agents to topical as well as large, complex and geometrically complex areas of the body or material surfaces, which are often used in biomedical and pharmaceutical fields, such as wound healing, drug delivery systems, and devices. Currently, there are two main types of spray systems: non-pressurized and pressurized, which are clinically used or studied as delivery platforms for therapeutic agents. With non-pressurized systems, the dose of active ingredient is delivered through a metered-dose with a pump. In contrast, pressurized systems, also known as aerosols, depend on the power of compressed or liquefied gas to expel the ingredients from the container. These non-pressurized spray types are attractive systems for topical and systemic delivery of therapeutic agents due to their dose accuracy, reproducibility, and inexpensive and convenient characteristics, allowing for easy and ready to use by patients as well as physicians in any setting. Thus, these spray techniques have been explored as therapeutic delivery systems via localized routes of administration, including nasal, oral and dermal. Liquid sprays are effective in delivering relevant dosage of therapeutic agents via the nasal cavity, but often suffer from poor retention, dripping from the nose or draining rapidly followed by swallowing, which result in reduced bioavailability and impacting therapeutic response. Aerosol spray systems have the potential to address these issues by offering rapid drug delivery to the respiratory tract while increasing the bioavailability of the drugs and minimizing the exposure of unaffected organs and tissues to the drugs. Besides aerosols, recently, there has been growing interest in the use of fiber-based scaffolds, such as 1D, 2D, and 3D micro- and nanofibers, as carriers for drug delivery due to their remarkable advantages in controlling drug release rate by varying composition and structure (e.g., micro- or macro-), allowing for low initial drug release burst rate compared to spherical carriers and controlled zero-order drug release profiles. Moreover, fiber morphologies provide distinct features, including high porosity, large surface area-to-volume ratio, and case of functionalization with bioactive molecules, such as enzymes and growth factors, making them promising candidates as scaffolds for tissue engineering and regenerative medicine. Currently, however, there are no available options or alternatives that are relatively simple, safe, and effective to fabricate fibers in the form of sprays without the use of an electric field or compressed gas source. This limitation is evident despite the potential for such systems as tissue adhesives and coatings in minimally invasive surgery for hemostasis and as wound and burn coating materials to deliver protection and therapeutics in non-surgical settings, such as in field needs and emergencies.

Silk fibroin protein is a natural protein biopolymer derived from the cocoons of domesticated *Bombyx mori* silkworms and can be processed into various material scaffolds, including films, nanofibers, sponges, particles, microneedles, and hydrogels, which can be utilized in biomedical applications, such as tissue engineering scaffolds and implantable devices. Silk also has favorable characteristics for the delivery of therapeutic agents to the body, such as biocompatibility with low immunogenicity, biodegradability, case of chemical modifications, self-assembling properties, edible nature, and controlled and sustained release of a wide range of bioactive molecules, such as genes, small molecules, and drugs. For drug delivery, rapid sol-gel transitions of silk have been developed using sonication, surfactants, and polyethylene glycol (PEG), where this physical phase transition arises from a combination of inter- and intramolecular interactions, including hydrophobic interactions, hydrogen bonding, and electrostatic interactions, leading to the acceleration of silk self-assembly into β-sheet crystalline structures that result in physical cross-linking as well as insolubility in aqueous systems. Based on this principle, silk has been prepared into microparticles by various approaches, such as spray drying, microfluidics, emulsification, organic solvent-assisted self-assembly, and mixing of silk solution with PEG via pipetting. However, effective spray delivery of drugs formulated as an aerosol in situ is technically challenging due to difficulties in inducing instantaneous conformational transitions of silk aqueous solutions from random coils to β-sheets at ambient conditions; mimicking silkworm and spider processes. In addition, the high molecular weight of silk causes difficulties in controlling the formation of silk particles, and in particular, silk fibroin is prone to self-assemble into gels when exposed to shear force, pH change, heat, organic solvent, or salts. Therefore, in situ, simple and robust fabrication of silk aerosols remain a major challenge.

Besides in situ fabrication of aerosols, the in situ instantaneous fabrication of silk fibers at ambient conditions remains unanswered. Up to now, most efforts have focused on the use of wet or dry spinning or electrospinning to produce silk fibers, with emphasis on reproducing the mechanical properties of natural silks, and relatively little attention has been given to recreating silk protein fibers with hierarchical structure in a simple and effective manner, which is a key feature of natural silks. Moreover, wet and dry spinning techniques generally involve the use of organic solvents, and electrospinning also requires a strong electric field and conductive target, which limit practical utility as an in situ fiber spraying system.

A variety of artificial silk spinning approaches have been attempted to mimic the natural spinning process found in silkworms and spiders, yet a key element is missing to enable instantaneous silk fiber formation with hierarchical structure under physiological and ambient conditions without post-treatment procedures. A need exists for methods, spray devices, and kits capable of producing silk fibroin aerosols and/or fibers without the aforementioned shortcomings.

SUMMARY

In an aspect, the present disclosure provides a method of making in situ silk fibroin aerosols and/or fibers. The method includes: rapidly mixing a silk fibroins solution and a beta sheet initiation solution under shear force to provide a mixed solution having rapidly initiation formation of beta sheet crystal structure; and rapidly expanding the mixed solution, thereby providing elongation force to the mixed solution and making the silk fibroin aerosols and/or fibers. The silk fibron solution and the beta sheet inititation solution are prevented from contacting one another prior to the rapidly mixing. The silk fibroin solution contains fragments having a molecular weight distribution. The beta sheet initiation solution include a hygroscopic polymer with a molecular weight of between 7.5 kDa and 15.0 kDa. The rapidly mixing and rapidly expanding steps occur within one second of one another. The method makes the silk fibroin aerosols when the molecular weight distribution is below an aerosol-fiber threshold. The method makes the silk fibroin fibers when the molecular weight distribution is above an aerosol-fiber threshold.

In another aspect, the present disclosure provides a spray device for making in situ silk fibroin aerosols and/or fibers. The spray device includes a first reservoir, a second reservoir, a fluid pathway, and a pump. The fluid pathway includes a rapid shear mixing chamber and a rapid expansion chamber. The first reservoir contains a silk fibroin solution. The silk fibroin solution contains fragments having a molecular weight distribution. The second reservoir contains a beta sheet initiation solution. The pump is operatively coupled to the first reservoir, the second reservoir, the shear mixing chamber, and the elongational chamber, such that when the pump is activated, the spray device does the following: rapidly mixes the silk fibroin solution and the beta sheet initiation solution under shear force to provide a mixed solution having rapidly initiation formation of beta sheet crystal structure; and rapidly expand the mixed solution, thereby providing epongation force to the mixed solution and making the silk fibroin aerosols and/or fibers. The pump rapidly mixes and rapidly expand within 1 second of one another. The spray device makes the silk fibroin aerosols when the molecular weight distribution is below an aerosol-fiber threshold. The spray device makes the silk fibroin fibers when the molecular weight distribution is above the aerosol-fiber threshold.

In another aspect, the present disclosure provides a kit. The kit includes a first reservoir and a second reservoir. The first reservoir include a silk fibroin solution. The second reservoir includes a beta sheet initiation solution. The kit maintains physical separation of the silk fibroin solution and the beta sheet initiation solution. The first and second reservoirs are accessible to allow their contents to be removed and rapidly mixed. The silk fibroin solution contains fragments having a molecular weight distribution that is above or below an aerosol-fiber threshold.

Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DETAILED DESCRIPTION

Definitions

Figure 1:
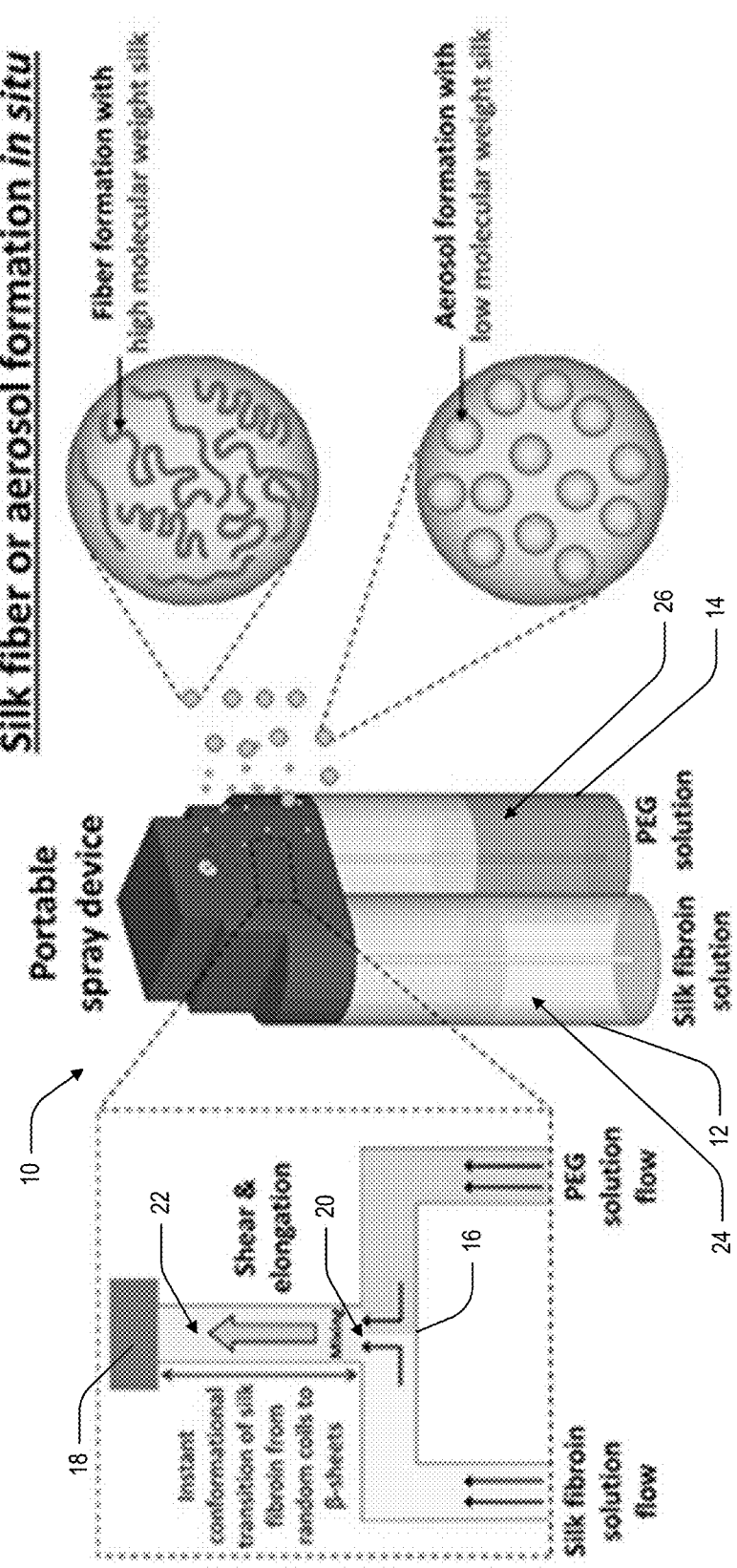
FIG. 1 is a schematic representation of a spray device and its function, in accordance with aspects of the present disclosure.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" are used as equivalents and may be understood to permit standard variation as would be understood by those of ordinary skill in the art; (v) where ranges are provided, endpoints are included; (vi) when used herein, the term "comprising" also expressly contemplates the use of the terms "consisting essentially of" and "consisting" in its place, unless the context clearly dictates otherwise, using the definitions consistent with United States patent law.

Biocompatible: the term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, including but not limited to, less than or equal to 15%, 10%, 5%, or 1% cell death.

Biodegradable: as used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid) (PLA), poly(glycolic acid) (PGA), poly (lactic-co-glycolic acid) (PLGA), and copolymers with PEG, polyanhydrides, poly(ortho) esters, polyesters, polyurethanes, poly(butyric acid), poly(valeric acid), poly (caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Composition: as used herein, may be used to refer to a discrete physical entity that comprises one or more specified components. In general, unless otherwise specified, a composition may be of any form—e.g., gas, gel, liquid, solid, etc. In some embodiments, "composition" may refer to a combination of two or more entities for use in a single embodiment or as part of the same article. It is not required in all embodiments that the combination of entities result in physical admixture, that is, combination as separate co-entities of each of the components of the composition is possible; however many practitioners in the field may find it advantageous to prepare a composition that is an admixture of two or more of the ingredients in a pharmaceutically acceptable carrier, diluent, or excipient, making it possible to administer the component ingredients of the combination at the same time.

Fibroin: As used herein, the term "fibroin" includes silkworm silk fibroin and insect or spider silk protein (Lucas et al, Adv. Protein Chem 13:107-242 (1958)). Any type of silk fibroin can be used according to aspects of the present invention. There are many different types of silk produced by a wide variety of species, including, without limitation: Antheraca mylitta; Antheraca pernyi; Antheraca yamamai; *Galleria mellonella; Bombyx mori; Bombyx* mandarina;

*Galleria mellonella*; Nephila clavipes; Nephila *senegalensis*; Gasteracantha mammosa; Argiope *aurantia*; Araneus diadematus; *Latrodectus* geometricus; Araneus bicentenarius; Tetragnatha *versicolor*; Araneus *ventricosus*; Dolomedes *tenebrosus*; Euagrus chisoseus; Plectreurys *tristis*; Argiope trifasciata; and Nephila *madagascariensis*. In some embodiments, fibroin is obtained from a solution containing a dissolved silkworm silk or spider silk. The silkworm silk protein is obtained, for example, from *Bombyx mori*, and the spider silk is obtained from Nephila clavipes. Other silks include transgenic silks, genetically engineered silks (recombinant silk), such as silks from bacteria, yeast, mammalian cells, transgenic animals, or transgenic plants, and variants thereof. See for example, WO 97/08315 and U.S. Pat. No. 5,245,012, content of both of which is incorporated herein by reference in its entirety. In some embodiments, silk fibroin can be derived from other sources such as spiders, other silkworms, bees, synthesized silk-like peptides, and bioengineered variants thereof. In some embodiments, silk fibroin can be extracted from a gland of silkworm or transgenic silkworms. See for example, WO2007/098951, content of which is incorporated herein by reference in its entirety. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" and "Gly-rich" hydrophobic blocks are typically separated by segments of amino acids with bulky side-groups (e.g., hydrophilic spacers). In some embodiments, core repeat sequences of the hydrophobic blocks of fibroin can be represented by the following amino acid sequences and/or formulae: (GAGAGS) 5-15 (SEQ ID NO: 1); (GX) 5-15 (X=V, I, A) (SEQ ID NO: 2); GAAS (SEQ ID NO: 3); (S1-2A11-13) (SEQ ID NO: 4); GX1-4 GGX (SEQ ID NO: 5); GGGX (X=A, S, Y, R, D V, W, R, D) (SEQ ID NO: 6); (S1-2A1-4) 1-2 (SEQ ID NO: 7); GLGGLG (SEQ ID NO: 8); GXGGXG (X=L, I, V, P) (SEQ ID NO: 9); GPX (X=L, Y, I); (GP (GGX) 1-4 Y) n (X=Y, V, S, A) (SEQ ID NO: 10); GRGGAn (SEQ ID NO: 11); GGXn (X=A, T, V, S); GAG (A) 6-7GGA (SEQ ID NO: 12); and GGX GX GXX (X=Q, Y, L, A, S, R) (SEQ ID NO: 13). In some embodiments, a fibroin peptide can contain multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide can contain between 4-17 hydrophobic blocks. In some embodiments of the invention, a fibroin peptide comprises at least one hydrophilic spacer sequence ("hydrophilic block") that is about 4-50 amino acids in length. Non-limiting examples of the hydrophilic spacer sequences include: TGSSGFGPYVNGGYSG (SEQ ID NO: 14); YEYAWSSE (SEQ ID NO: 15); SDFGTGS (SEQ ID NO: 16); RRAGYDR (SEQ ID NO: 17); EVIVIDDR (SEQ ID NO: 18); TTIIEDLDITIDGADGPI (SEQ ID NO: 19) and TISEELTI (SEQ ID NO: 20). In certain embodiments, a fibroin peptide can contain a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences. In some embodiments, a fibroin peptide suitable for the present invention contains no spacer. Silks are generally fibrous proteins and characterized by modular units linked together to form high molecular weight, highly repetitive proteins.

These modular units or domains, each with specific amino acid sequences and chemistries, are thought to provide specific functions. For example, sequence motifs such as poly-alanine (poly A) and poly-alanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of different components in various silk structures whose positioning and arrangement are tied with the end material properties of silk-based materials (reviewed in Omenetto and Kaplan (2010) Science 329:528-531). Also see: WO 2011/130335 (PCT/US2011/032195), the contents of which are incorporated herein by reference.

Improve, increase, or reduce: as used herein or grammatical equivalents thereof, indicate values that are relative to a baseline measurement, such as a measurement in a similar composition made according to previously known methods.

Physiological conditions: as used herein, has its art-understood meaning referencing conditions under which cells or organisms live and/or reproduce. In some embodiments, the term refers to conditions of the external or internal mileu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Reference: as used herein describes a standard or control relative to which a comparison is performed. For example, in some embodiments, a material, article, additive, entity or other sample, sequence or value of interest is compared with a reference or control material, article, additive, entity or other sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Substantially: as used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, New Jersey (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24:401 (2003); see also Sashina et al., Russ. J. Appl. Chem., 79:869 (2006)).

Silk is naturally produced by various species, including, without limitation: Antheraca mylitta; Antheraca pernyi; Antheraca yamamai; *Galleria mellonella; Bombyx mori; Bombyx* mandarina; *Galleria mellonella*; Nephila clavipes; Nephila *senegalensis*; Gasteracantha mammosa; Argiope *aurantia*; Araneus diadematus; *Latrodectus* geometricus; Araneus bicentenarius; Tetragnatha *versicolor*; Araneus *ventricosus*; Dolomedes *tenebrosus*; Euagrus chisoseus; Plectreurys *tristis*; Argiope trifasciata; and Nephila *madagascariensis*.

As is known in the art, silks are modular in design, with large internal repeats flanked by shorter (–100 amino acid) terminal domains (N and C termini). Naturally-occurring silks have high molecular weight (200 to 350 kDa or higher) with transcripts of 10,000 base pairs and higher and >3000 amino acids (reviewed in Omenatto and Kaplan (2010) Science 329:528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules.

In general, silk fibroin for use in accordance with the present invention may be produced by any such organism, or may be prepared through an artificial process, for example, involving genetic engineering of cells or organisms to produce a silk protein and/or chemical synthesis. In some embodiments of the present invention, silk fibroin is produced by the silkworm, *Bombyx mori*. Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of nonstructural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the *Bombyx mori* fibroin light-chain-encoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained from the cocoon of *Bombyx mori*. In some embodiments, spider silk fibroins are obtained, for example, from Nephila clavipes. In some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

In some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk fibroin materials explicitly exemplified herein were typically prepared from material spun by silkworm, *Bombyx mori*. Typically, cocoons are boiled in an aqueous solution of 0.02 M Na2CO3, then rinsed thoroughly with water to extract the glue-like sericin proteins (this is also referred to as "degumming" silk). Extracted silk is then dissolved in a solvent, for example, LiBr (such as 9.3 M) solution at room temperature. A resulting silk fibroin solution can then be further processed for a variety of applications as described elsewhere herein.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

As used herein, the phrase "silk fibroin fragments" refers to peptide chains or polypeptides having an amino acid sequence corresponding to fragments derived from silk fibroin protein or variants thereof. In the context of the present disclosure, silk fibroin fragments generally refer to silk fibroin peptide chains or polypeptides that are smaller than the naturally occurring full length silk fibroin counterpart, such that one or more of the silk fibroin fragments within a population or composition are less than 300 kDa. The provided silk fibroin fragments may be degummed under a specific condition (e.g., degumming time and atmospheric boiling temperature or a temperature ranging from 90° C. to 110° C.) to produce silk fibroin fragments having a desired molecular weight. In some embodiments, a silk solution may be produced having silk fibroin with a molecular weight that ranges from 3.5 kDa to 300 kDa, from 50 kDa to 120 kDa, or from 120 kDa to 300 kDa. In some embodiments, the molecular weight is at least 3.5 kDa, or at least 5 kDa, or at least 10 kDa, or at least 20 kDa, or at least 30 kDa, or at least 40 kDa, or at least 50 kDa, or at least 60 kDa, or at least 70 kDa, or at least 80 kDa, or at least 90 kDa, to less than 100 kDa, or less than 110 kDa, or less than 120 kDa, or less than 130 kDa, or less than 140 kDa, or less than 150 kDa, or less than 200 kDa, or less than 250 kDa, or less than 300 kDa. In some cases, the silk fibroin can be a low molecular weight silk fibroin, such as is described in WO 2014/145002, which is incorporated herein in its entirety by reference.

This disclosure provides a method of making in situ silk fibron aerosols and/or fibers. The method includes rapidly mixing a silk fibroin solution and a beta sheet initiation solution under shear force to form a mixed solution. The method also includes rapidly expanding the mixed solution. The rapidly mixing and rapidly expanding steps occur within 1 second of one another. As used herein, the concepts of rapidly mixing and rapidly expanding could also be conceived as mixing under shear and elongational flow. For the avoidance of doubt, the specific terminology is not intended to be limiting and the relevant technical concepts (i.e., the importance of shear force and rapid mixing in forming beta sheet crystal structure quickly, the importance of rapid expanding or elongational flow in aligning globules to form fibers or breaking off globules to form aerosols) would be understood by those having ordinary skill in the silk fibroin handling arts.

The rapidly mixing under shear force can be achieved by a variety of fluid pathways. As one non-limiting example, the rapidly mixing can be done via a drawing pump that pulls the silk fibron solution and the beta sheet initiation solution from their respective reservoirs into a T- or Y-joint, where the solutions undergo rapid mixing. The drawing can be done via commercially-available spray pumps or atomizers. As another non-limiting example, the rapidly mixing can be done via pressurizing reservoirs that contain the silk fibroin solution and the beta sheet initiation solution to push the solutions into a T- or Y-joint, where the solutions undergo rapid mixing. The pressurizing can be done via one-way valves and pliable reservoirs, such as the technology that is presently used in conventional nose-spray devices. The specific means of rapid mixing is not intended to be limiting to the present invention, so long as the speed of mixing and degree of shear force are adequate.

As used herein, rapidly mixing and rapidly expanding are defined in terms of being adequately rapid to support the formation of the desired aerosols and/or fibers. The rapidly mixing under shear force rapidly initiates formation of beta sheet crystal structure within the mixed solution. As used herein, rapidly initiating formation of beta sheet crystal structure is defined in terms of being adequately rapid to support formation of the desired aerosols and/or fibers. If the other necessary conditions of aerosol and/or fiber formation are met (i.e., the silk fibroin solution and beta sheet initiation solution are capable of aerosol and/or fiber formation and the mixing chamber/device/region provides adequate shear force), and if the solutions are mixed to form a mixed solution having initiated formation of beta sheet crystal structure and the mixed solution is expanded, and if this process fails to generate the desired aerosols and/or fibers, then one or more of the mixing, beta sheet initiation (which is dependent on the mixing and shear force), and expanding did not occur rapidly enough. Without wishing to be bound by any particular theory, it is believed that certain solution conditions may require different rapidity with respect to these processes and a skilled artisan would recognize the metes and bounds of whether a given mixing, beta sheet initiation, or expanding is rapid or non-rapid as defined herein by sampling the variable space with solutions that are known to generate the desired aerosols and/or fibers.

In order to achieve the rapid formation of beta sheet crystal structure, the silk fibroin solution and the beta sheet initiation solution must be kept physically separate from one another prior to the mixing. The mixing and the shear force are simultaneous. The combination of contacting the silk fibroin solution with the hygroscopic polymer (which facilitates formation of beta sheet structure) and the shear force (which facilitates formation of beta sheet structure) facilitate forming beta sheet crystal structure with sufficient rapidity to allow formation of aerosols and/or fibers.

The beta sheet initiation solution contains a hygroscopic polymer having a molecular weight that support formation of the desired aerosols and/or fibers. Without wishing to be bound by any particular theory, it is believed that the molecular weight of the hygroscopic polymer impacts the ability of the silk fibroin to form the desired aerosols and/or fibers. The hygroscopic polymer can have a weight or number average molecular weight of at least 7.5 kDa, at least 8.0 kDa, at least 8.5 kDa, at least 9.0 kDa, or at least 9.5 kDa. The hygroscopic polymer can have a weight or number average molecular weight of at most 15.0 kDa, at most 14.0 kDa, at most 13.0 kDa, at most 12.5 kDa, at most 12.0 kDa, at most 11.5 kDa, at most 11.0 kDa, or at most 10.5 kDa. The hygroscopic polymer can be selected from those understood to be compatible with the methods described herein, such as polyethylene glycol (PEG), polyethylene oxide (PEO), polyvinyl alcohol (PVA), and the like. In some cases, the hygroscopic polymer is PEG. The beta sheet initiation solution can include the hygroscopic polymer in an amount by weight of at least at least 1.0%, at least 2.0%, or at least 3.0% and at most 40.0%, at most 30.0%, at most 20.0%, or at most 10.0%.

The silk fibroin solution can include silk fibroin in an amount by weight of at least 1.0%, at least 2.0%, or at least 3.0% and at most 40%, at most 30%, at most 20%, or at most 10%.

The mixed solution (by virtue of the concentrations of the respective solutions and their proportions) can include the silk fibroin in an amount by weight of at least 0.5%, at least 1.0%, at least 1.5%, or at least 2.0% and at most 30.0%, at most 25.0%, at most 20.0%, at most 15.0%, at most 10.0%, or at most 5.0%. The mixed solution can include the hygroscopic polymer in an amount by weight of at least 0.5%, at least 1.0%, at least 1.5%, or at least 2.0% and at most 30.0%, at most 25.0%, at most 20.0%, at most 15.0%, at most 10.0%, or at most 5.0%. The rapidly mixing (and thus the mixed solution) can involve a ratio by volume of silk fibroin solution to beta sheet initiation solution of at least 4:1, at least 3:1, at least 2:1, at least 1:1, at least 1:2, or at least 1:3 and at most 1:4, at most 1:3, at most 1:2, at most 1:1, at most, 2:1, or at most 3:1. In some cases, the rapidly mixing involves equal amounts of silk fibroin solution and beta sheet initiation solution.

The mixed solution can have a pH of between 2 and 9. In some cases, the mixed solution can have a pH of at least 2, at least 3, at least 4, at least 5, at least 6, at least 7. In some cases, the mixed solution can have a pH of at most 9, at most 8, at most 7, at most 6, at most 5, or at most 4.

As used herein, reference to a molecular weight distribution being above or below a given threshold can refer to a weight average molecular weight or a number average molecular weight being above or below a given threshold. In some cases, reference to a molecular weight distribution being above or below a given threshold can refer to a weight or number average molecular weight being roughly equivalent to a given molecular weight threshold and a polydispersity being above or below a given polydispersity threshold. In other words, reference to a molecular weight distribution being above or below a given threshold generally refers first to the weight or number average molecular weight being above or below a given molecular weight threshold and then in cases where the weight or number average molecular weight is roughly equal to the given molecular weight threshold refers second to the polydispersity being above or below a given polydispersity threshold. In some cases, the aerosol-fiber threshold is a number average molecular weight of 120 kDa, 110 kDa, 100 kDa, 90 kDa, 75 kDa, 70 kDa, 60 kDa, 50 kDa, or 40 kDa.

In some cases, the molecular weight distribution being above or below a given threshold refers to a length of time for a given heating step in the silk fibroin solution preparation process, for example, the degumming boiling time. In some cases, the aerosol-fiber threshold can be defined in terms of a degumming boiling time threshold. In these cases, the degumming boiling time threshold can be 45 minutes, 50 minutes, 55 minutes, 60 minutes, 75 minutes, 90 minutes, or 120 minutes.

Applicant submits that the specific aerosol-fiber threshold can be impacted by environmental factors. Unless indicated otherwise, the performance characteristics described herein (i.e., situations where fibers are formed instead of aerosols and vice versa) are described with respect to typical ambient conditions in a laboratory environment, such as generally atmospheric pressure and generally room temperature (i.e., 15-25° C.). In some cases, the performance characteristics are described with respect to physiological conditions. In some cases, the performance characteristics are applicable to both ambient and physiological conditions.

Referring to FIG. 1, this disclosure provides a spray device 10. The spray device 10 includes a first reservoir 12, a second reservoir 14, a fluid pathway 16, and a pump 18 (or portion thereof—in one specific instance, the part denoted by reference numeral 18 is a one-way valve that forms part of a pump, the other part of which is formed by flexible reservoirs that allow manual increase of pressure within them to facilitate forcing solutions out of the reservoirs). The fluid pathway 16 includes a rapid shear mixing chamber 20 and a rapid expansion chamber 22. In some cases, the rapid shear mixing chamber 20 and the rapid expansion chamber 22 are a single chamber/region/space/volume that facilitates both the mixing under shear force and the expansion/elongational force. The first reservoir 12 includes a silk fibroin solution 24. The second reservoir 14 includes a beta sheet initiation solution 26.

When the pump 18 is activated, the spray device executes the method described above.

As used herein, the term "pump" broadly refers to a liquid pumping mechanism, and includes, among others: commercially available atomizer pumps; commercially available spray caps; one-way valves paired with flexible reservoir housings, such as are used in older nasal spray bottles; and the like. The pump 18 can be a manual pump. The pumping mechanism can be drawing liquid through the fluid pathway 16. The pumping mechanism can be forcing liquid through the fluid pathway 16.

The forces and/or pressures generated by the pump are balanced with the dimensions of the fluid pathway 16 to ensure that the necessary shear and elongational forces are being provided. A skilled artisan in fluid dynamics would recognize that a variety of different approaches can be taken to balance these forces and successful formation of aerosols and/or fibers under known reaction conditions is one benchmark for establishing that the spray device 10 and pump 18 produce the necessary forces.

The spray device 10 does not include a pressurized or compressed gas source and the method does not use pressurized or compressed gas, aside from that generated by a manual pump.

The spray device 10 does not include an electric field generator and does not require a conductive target for receiving generated fibers. The methods do not use electric fields or conductive targets.

This disclosure provides a kit. In general, the kit can include all portions of the spray device 10, but without the fluid pathway 16 and the pump 18.

In some cases, the kit includes the rapid shear mixing chamber 20. In some cases, the kit includes the rapid expansion chamber 22.

In some cases, the kit is adapted to be engaged by a commercially-available atomizer and/or pump spray cap and/or other rapid expansion pump. In some cases, the kit can be in the form of a replaceable cartridge.

Some features of the present disclosure were described in greater detail with respect to the method, but those features are also expressly contemplated as being usable and combinable with all aspects described with respect to the spray device and the kit. The same is true with respect to features described in greater detail with respect to the spray device or the kit. All aspects of the method are combinable with all aspects of the spray device and vice versa. All aspects of the method or spray device are combinable with all aspects of the kit and vice versa.

Example 1

Where the characteristics of fiber are discussed in this Example, that characterization is based on some form of image, which may or may not be included in this patent application. If an image is desired for patent examination, it can be provided to an examiner. If an image is needed for a reader, there is a journal article that will publish near the time that this patent application is filed and many of the images can be found in that article. For the avoidance of doubt, the peer-reviewed journal article being referenced will contain the same experimental section as this example.

Preparation of Aqueous Silk Fibroin Solutions: 5 g of cut cocoons of silkworms (Tajima Shoji Co., Ltd, Yokohama, Japan) were boiled in 2 L of 0.02 M sodium carbonate (Na2CO3, Sigma-Aldrich, St. Louis, MO) solution for 5, 30, or 180 minutes. The degummed silk fibers were rinsed with DI water three times and dried in a fume hood overnight. The dried fibers were dissolved in 9.3 M lithium bromide (LiBr, SigmaAldrich, St. Louis, MO) solution at 60° C. for 4 or 6 h depending on the degummed time. Then, the silk solution was dialyzed against DI water using standard grade regenerated cellulose dialysis membrane (MWCO: 3500 kD, Spectra/Por®3 Standard RC Tubing, Spectrum Laboratories Inc., Rancho Dominguez, CA) for 3 days with six changes of DI water. The silk solution was then centrifuged twice at 9,000 rpm at 4° C. for 20 minutes to remove impurities. The concentration of resulting silk solutions (pH=6) was determined by weighing the mass of a dried sample after drying a known volume of aqueous silk solution at 60° C. overnight.

Preparation of PEG10k Solutions: 20% (w/v) PEG10k (Mw=10 kDa, SigmaAldrich, St. Louis, MO) aqueous solution (pH=3 and 8) was prepared by dissolving 20 g of PEG10k in distilled water, where the final desired pH was adjusted using hydrochloric acid (HCl) or sodium hydroxide (NaOH) solution. 19.54 g of citric acid monohydrate (Mw=210.14 g mol$^{-1}$, SigmaAldrich, St. Louis, MO) and 2.06 g of sodium citrate tribasic dihydrate (Mw=294.12 g mol$^{-1}$, SigmaAldrich, St. Louis, MO) were dissolved in 80 mL of distilled water and then the final solution pH was adjusted to 3, followed by adding distilled water until the final volume was 100 mL to prepare 1 M sodium citrate buffer solution at pH=3. Then, 20 g of PEG10k was dissolved in this buffer solution.

Fabrication of a Spray Device: A customized spray device was used to perform experiments. A fine mist mini spray bottle (volume: 10 ml, material: polyethylene terephthalate (PET), height: 7.6 cm) with the pump was purchased from Amazon.com, Inc. . . . Rubber tubes, 90° elbow connectors, and tee connectors were purchased from mcmaster.com.

In Situ Fabrication of Silk Fibers Using Spray Devices: To investigate the effect of PEG concentration, pH, and ionic strength on fiber formation, the concentration of PEG10k stock solutions was varied. For 20% (w/v) PEG10k dissolved in distilled water at pH=3 and 8, the concentration was diluted to 4, 8, and 16%. For 20% (w/v) PEG10k dissolved in 1M sodium citrate buffer solution at pH=3, the concentration was diluted to 4, 8, and 16%. To fabricate silk fibers, 3 mL of PEG10k solution diluted was loaded into one container of the spray device and 3 mL of 4% silk solution boiled for 5 or 30 minutes was loaded into the other container. The fibers were instantly fabricated upon pressing the atomizer cap of the spray device.

In Situ Fabrication of Silk Aerosols Using Spray Devices: 3 mL of 20% PEG10k solution at pH=8 was loaded into one container of the spray device and 3 mL of 20% silk solution boiled for 180 minutes was loaded into the other container. The aerosols were instantly fabricated upon pressing the atomizer cap of the spray device.

Preparation of Drug-Loaded Silk Fibers and Aerosols: Rhodamine B (Mw=479.01 g mol$^{-1}$, SigmaAldrich, St.

Louis, MO) was used as a model drug to investigate drug loding in sprayed silk fibers and aerosols. Rhodamine B stock solution with a concentration of 1 mg mL$^{-1}$ was prepared in distilled water at pH=8. For the preparation of drug-loaded silk fibers, 250 µL of rhodamine B stock solution was mixed with 3 mL of 4% silk solution boiled for 30 minutes to obtain a weight ratio of 1:480 between rhodamine B and silk. This solution was then transferred to one container of the spray device, and 3 mL of 8% PEG10k solution dissolved in distilled water at pH=8 was transferred to the other container. The rodamine B-loaded fibers were instantly generated upon pressing the atomizer cap of the spray device. For the preparation of drug-loaded silk aerosols, 500 µL of rodamine B stock solution was mixed with 2 mL of 20% silk solution boiled for 180 minutes to obtain a weight ratio of 1:800 between rodamine B and silk. Then, this solution was loaded into one container of the spray device, and 2 mL of 20% PEG10k solution dissolved in distilled water at pH=8 was loaded into other container. The rodamine B-loaded aerosols were instantly produced upon pressing the atomizer cap of the spray device.

Confocal Laser Scanning Microscopy (CLSM): The distribution of rhodamine B molecules in sprayed silk fibers and aerosols was investigated using a TCS SP8 microscope (Leica Microsystems, Wetzlar, Germany).

Attenuated Total Reflectance-Fourier Transform Infrared Spectroscopy (ATR-FTIR): For ATR-FTIR measurement, silk fibers collected on Petri dishes were washed with DI water on the orbital shaker for 20 minutes two times. The fibers were then dried in a fume hood for 2 days. Secondary structures of silk fibers were examined in the amide I region (1600-1700 cm$^{-1}$) by averaging 32 scans with a resolution of 4 cm$^{-1}$ using a JASCO FTIR 6200 spectrometer (JASCO, Tokyo, Japan) with a MIRacle™ attenuated total reflection (ATR) with germanium crystal. Data analysis was carried out using the Fourier self-deconvolution (FSD) method in the Origin Software (OriginPro 2020, OriginLab, Northampton, MA).

Rheological Behavior of Silk and PEG10k Solutions: The rheological properties of silk and PEG 10k solutions used for spray experiments were investigated using a TA Instruments ARES-LS2 rheometer (TA Instruments, New Castle, DE) using a 25 mm stainless steel cone (angle: 0.0994 rad) and plate geometry. The viscosity was measured as a function of the shear rate in the range of 0.01-1000 s$^{-1}$.

Scanning Electron Microscopy (SEM): For SEM imaging of silk fibers, the fibers sprayed on Petri dish were washed with DI water on the orbital shaker for 20 minutes two times to remove the PEG. The samples were then dried in a fume hood for 2 days and attached to a SEM sample stub. For SEM imaging of the as-sprayed silk aerosols, the aerosols sprayed on Petri dish were dried in a fume hood for 2 days. The Petri dish was then cleaved and attached to the carbon tape on a SEM sample stub. For SEM imaging of silk aerosols without the PEG, the aerosols sprayed in a scintillation glass vial were transferred to the centrifuge tube for a tabletop centrifuge and centrifuged at room temperature at 13,000 rpm for 15 minutes two times. The precipitated particles were suspended with DI water and the particle suspension (10 µL) was directly dropped onto the cleaved Petri dish attached on a SEM sample stub and dried in a fume hood for 2 days. Prior to SEM characterization, all samples were sputter-coated with gold. The SEM images were taken using a Zeiss SEM (EVO MA10, Germany) with an acceleration voltage of 10 kV.

Optical Microscopy: Silk fibers fabricated using 4% silk solution degummed for 30 minutes and different concentrations of PEG10k solutions dissolved in sodium citrate buffer at pH=3 and distilled water at pH=3 were collected on Petri dishes and washed with DI water on the orbital shaker for 20 minutes two times to remove the PEG. The fiber samples were then characterized using an optical microscope (Axiovert S100, Zeiss).

Statistical Analysis: ATR-FTIR measuremt was performed on n=3 independent sample replicates at each condition. Average values and standard deviations were calculated for all samples to produce graphical figures. Two-way analysis of variance (ANOVA) with Tukey's post hoc test was performed using GraphPad prism (GraphPad Software, San Diego, CA) to determine the statistical significance (*$p<0.05$,  $p<0.01$, * $p<0.001$).

Results and Discussion

A spray pump that is connected to two tubes, where one tube draws silk solution and the other draws PEG solution, was designed for the in situ fabrication of silk fibers and aerosols (FIG. 1). Silk fibroin aqueous solutions can be formed into microparticles when the silk solution is mixed with PEG solution via pipetting at room temperature. This is due to the ability of PEG to remove water from the silk and induce the hydrophobic regions of silk fibroin to interact and fold, leading to a structural change from random coils to β-sheets. However, this pipette-based mixing technique fostered only slow silk microparticle formation, i.e., after mixing the solutions an incubation time of 30 minutes or more was required to form particles, insufficient for the goals of the present study. The advantage of using a spray device to mix silk and PEG solutions over using a pipette is that the spray device can instantaneously apply high shear forces to the mixture, similar to the natural spinning processes observed in spiders and silkworms. When the atomizer cap of the spray pump was pressed, the hydraulic pressure generated in the spray containers resulted in the immediate structural transition of the silk from random coils to β-sheets right before spraying through the mixing of silk and PEG solutions under shear and elongational flow in the mixing tube, enabling the silk to be sprayed as fibers or aerosols in situ.

Table 1 summarize the spray formulations used in the present study. In the case of silk fibroin, longer DT led to lower average molecular weight distribution of silk molecules and vice versa. The number average molecular weight of silk degummed for 5, 30 and 180 minutes were above 200, around 160, and around 30 kDa, respectively, according to our previous data determined by sodium dodecyl sulfate-polyacrylamide gel electrophoresis (SDS-PAGE) analysis. The viscosity of the silk and PEG solutions is an important factor since the formulations require a low enough viscosity to flow easily in the tube with an inner diameter of 1.8 mm for the spray device. The viscosity profiles of the solutions had shear thinning behavior except for the silk solutions of 5 minutes DT, which showed shear thickening behavior at low shear rates followed by the shear thinning behavior above 0.032 s$^{-1}$, similar to the rheological characteristics of native spider and silkworm spinning dopes.

TABLE 1

Conditions of silk fibroin and PEG10k solutions used for spray formulations.

| | | | | Spray formulation | | |
| | | Silk | | | | |
| | Degumming time | Average molecular | | | PEG10k | |
| Sample | (DT, minutes) | weight (kDa) | Concentration (%, w/v) | Concentration (%, w/v) | Solution condition | Spray result |
|---|---|---|---|---|---|---|
| 1 | 5 | >200 | 4 | 4 | Dissolved in 1M sodium citrate buffer at pH 3 | Macroscale fibers |
| 2 | | | | 8 | | Macroscale fibers |
| 3 | | | | 16 | | Macroscale fibers |
| 4 | 5 | >200 | 4 | 4 | Dissolved in distilled water at pH 3 | Spider web-like fiber networks |
| 5 | | | | 8 | | Macroscale fibers |
| 6 | | | | 16 | | Macroscale fibers |
| 7 | | | | 4 | Dissolved in distilled water | Macroscale fibers |
| 8 | 5 | >200 | 4 | 8 | at pH 8 | Macroscale fibers |
| 9 | | | | 16 | | Macroscale fibers |
| 10 | 30 | ~160 | 4 | 4 | Dissolved in 1M sodium citrate buffer at pH 3 | Microscale fibers with local networks |
| 11 | | | | 8 | | Spider web-like fiber networks |
| 12 | | | | 16 | | Macroscale fibers |
| 13 | 30 | ~160 | 4 | 4 | Dissolved in distilled water at pH 3 | Scattered microscale fibers |
| 14 | | | | 8 | | Interconnected fibers |
| 15 | | | | 16 | | Spider web-like fiber networks |
| 16 | 180 | ~30 | 20 | 20 | Dissolved in distilled water at pH 8 | Aerosols |

Figure 2:
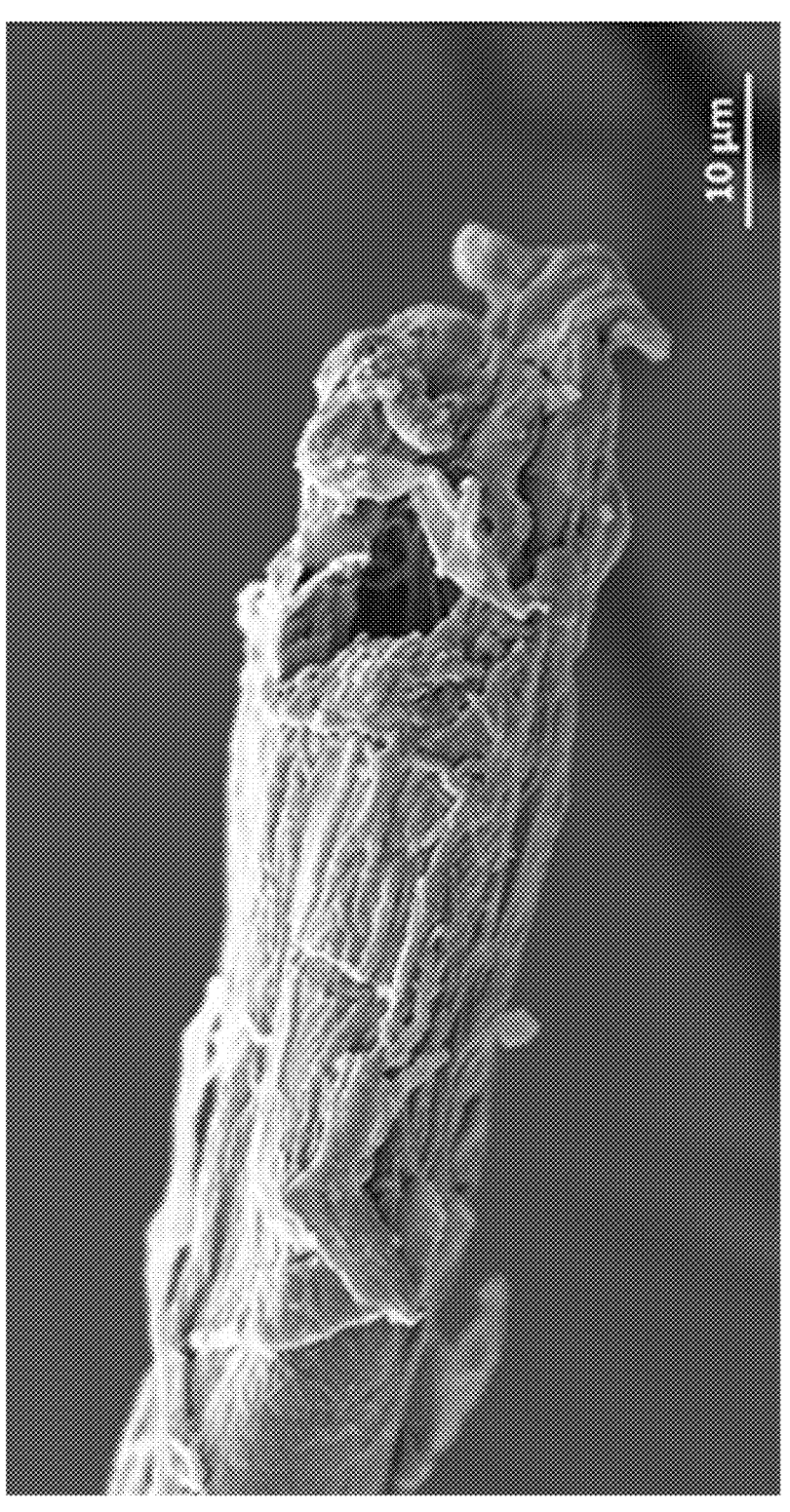
FIG. 2 is a scanning electron microscopy (SEM) image of a spray fiber consisting of aligned silk nanofibrils along the fiber axis, as shown in Example 1.
Figures 3, 4, 5, 6:
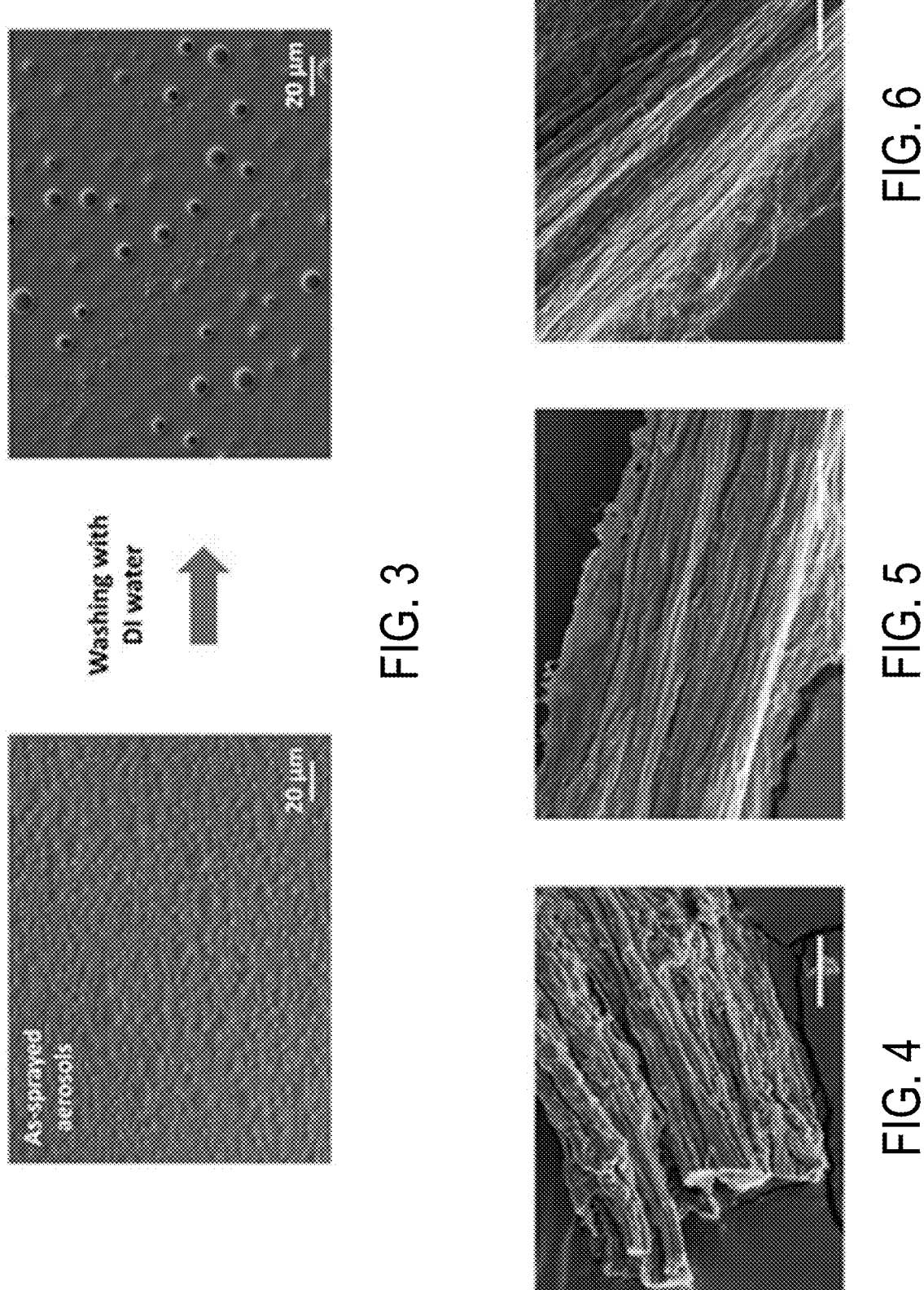
FIG. 3 shows SEM images of as-sprayed aerosols collected on a Petri dish (left) and those aerosols after washing with deionized (DI) water (right), as shown in Example 1.
FIG. 4 is an SEM image of sprayed fibers composed of hierarchically aligned silk nanofibrils, made from sample 3 from Table 1, as shown in Example 1.
FIG. 5 is an SEM image of sprayed fibers composed of hierarchically aligned silk nanofibrils, made from sample 6 from Table 1, as shown in Example 1.
FIG. 6 is an SEM image of sprayed fibers composed of hierarchically aligned silk nanofibrils, made from sample 9 from Table 1, as shown in Example 1.

The key parameter for fiber or aerosol morphologies via the spray was the molecular weight of the silk. When silk solutions of 5 and 30 minutes DT, i.e., relatively high molecular weight when compared to that of silk solutions of 180 minutes DT, were mixed with PEG10k solutions, silk fibers were produced. As-sprayed fibers were collected on a Petri dish (an image of this can be provided to a patent examiner, if needed, and can be found in a journal publication that contains the same experimental section as this example). The shape of deposition patterns of the droplets and the length of the silk fibers inside the droplets can be changed by adjusting the force to press the atomizer cap of the spray pump. For instance, the spherical shapes of droplets containing relatively short fibers were fabricated by pressing the atomizer cap to approximately 50% of fully pressing. In contrast, when the atomizer cap was fully pressed, elliptical shapes of droplets containing relatively long fibers were the result. This outcome could be associated with how much silk fibroin solution passes through the mixing tube of the spray device. Compared to a 50% pressed spray pump, fully pressed draws a larger amount of both silk and PEG10k solutions through the mixing tube at a given time, supporting the formation of longer fibers. For further investigation of fiber length, the as-sprayed fibers were washed with deionized (DI) water to remove the PEG, with fibers showing a length of ~4.5 cm. The fibers consisted of hierarchically aligned silk nanofibrils along the fiber axis (FIG. 2), similar to the natural silk fibers. On the other hand, when silk solutions of 180 minutes DT, i.e., low molecular weight of silk, were mixed with PEG10k solutions, silk microparticles were sprayed into the air, denoted as aerosols. FIG. 3 (left) shows a scanning electron microscopy (SEM) image of the as-sprayed aerosols collected on a Petri dish, where the diameter of the silk particles was in the size range of ~0.6-12 μm. When the collected aerosols were washed with DI water to remove the PEG, the spherical particle morphology was clearer (FIG. 3—right).

Initial screening experiments exhibited that only PEG solution with molecular weight of 10 kDa induced the fiber formation in situ upon spraying when it was mixed with silk solution of 30 minutes DT, whereas PEG solutions with molecular weight of 0.3, 3, 6, 20 kDa did not cause fiber formation. This result suggests that the chain length of PEG10k may be suitable for facilitating interactions with silk fibroin molecules under shear and elongational flow in the mixing tube of the spray device to instantly induce the conformation transition from random coils to β-sheets at room temperature, leading to the fiber formation. Thus, we focused on the use of PEG10k solution with different concentrations for further experiments. It is known that kosmotropic ions promote silk protein aggregation through salting-out. In addition, low pH and gradual removal of water enhance intra- and intermolecular hydrogen bonding of silk fibroin, yielding β-sheet crystalline structures. Based on these considerations, we explored the effects of silk molecular weight, i.e., DT, ionic strength, pH, and PEG10k concentration on the fabrication of silk fibers. To this end, 4% silk solutions of 5 minutes DT and a series of PEG10k dissolved in various solution conditions were prepared followed by spraying onto Petri dishes. When the 4% silk solution (pH=6) of 5 minutes DT and the 4, 8, or 16% PEG10k dissolved in 1M sodium citrate buffer at pH=3 were sprayed, well-defined macroscale silk fibers were generated, where the concentration of PEG10k had no significant effect on morphologies of the sprayed fibers. When spraying using the 4% silk solution of 5 minutes DT and the 4% PEG10k dissolved in distilled water at pH=3, spider web-like fiber networks with relatively small diameters were produced. Increasing the concentration of PEG10k to 16% led to the formation of general fiber morphologies, where a correlation between increasing diameter with increasing concentration was observed. In the case of spraying using the 4% silk solution of 5 minutes DT and the PEG10k dissolved in distilled water at pH=8, the tendency of the fiber diameter to increase was observed as the concentration of PEG10k was increased from 4 to 16%. SEM analysis of the sprayed silk fibers fabricated using the 4% silk solutions of 5 minutes DT and the PEG10k dissolved in different solution conditions revealed similar fiber morphologies, showing hierarchically aligned silk nanofibrils along the fiber axis (FIGS. 4-6). This result indicates that the microscale morphology of fibers fabricated using the silk solution of 5 minutes DT was not sensitive to the solution conditions of PEG10k.

Figure 7:
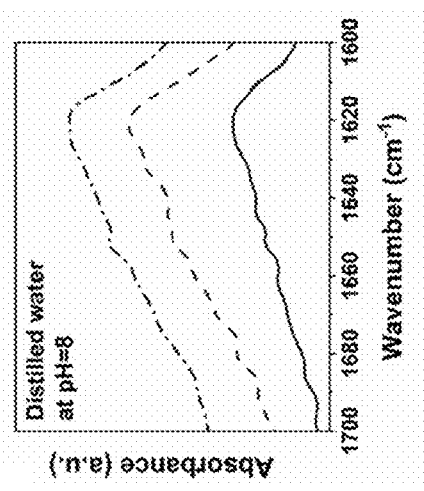
FIG. 7 are representative attenuated total reflection (ATR) Fourier transform infrared spectroscopy (FTIR) (ATR-FTIR) spectra of sprayed silk fibers, made under various conditions described in Example 1.
Figure 7:
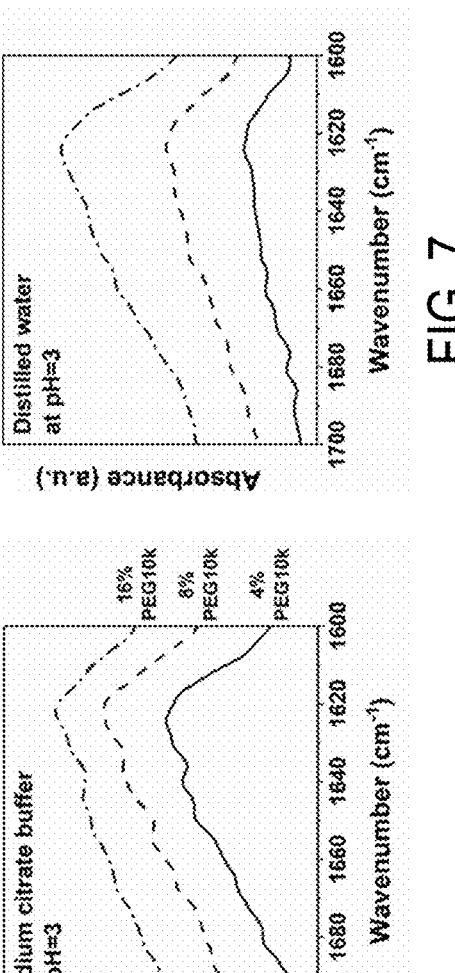
Figure 8:
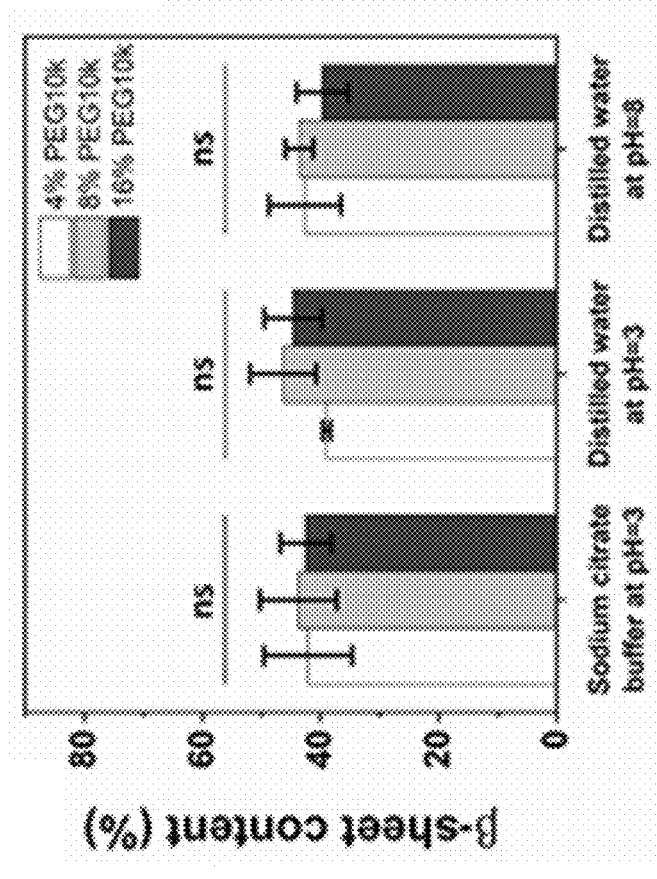
FIG. 8 is a plot showing the beta sheet content of silk fibers, as shown in Example 1.

Attenuated total reflectance-Fourier transform infrared spectroscopy (ATR-FTIR) was used to investigate the secondary structures of the sprayed fibers. Interestingly, regardless of solution conditions of PEG10k, all the fiber samples fabricated by the silk solution of 5 minutes DT showed similar FTIR spectra (FIG. 7). The fibers produced using 4, 8, and 16% PEG10k dissolved in 1M sodium citrate buffer at pH=3 showed a strong absorption peak at 1621 cm$^{-1}$ in the amide I region (1600-1700 cm$^{-1}$), indicating the dominant β-sheet crystalline structures (FIG. 7, left). After peak deconvolution, the β-sheet contents were 42.12±7.48, 43.78±6.5, and 42.5±4.29%, respectively, where there was no significant difference between the fiber samples (FIG. 8). For the fibers produced using 4, 8, and 16% PEG10k dissolved in both distilled water at pH=3 and 8, all samples also exhibited a strong absorption band around 1620 cm$^{-1}$ (FIG. 7, middle and right), and their β-sheet contents were in the range of 38-46%, where no significant difference was detected between the samples (FIG. 8).

Taken together, in the case of spraying using the silk solutions of 5 minutes DT, the concentration of PEG10k, buffer (i.e., ionic strength), and pH were not main factors for achieving silk fibers with hierarchical structures and enriched β-sheet conformations. The synergistic combination of the mixing of silk solution of 5 minutes DT with PEG10k solution having the concentration higher than the critical value (i.e., 4%) and the shear and elongational flow induced by the spray pump were the driving forces to instantly induce silk structural transition from random coils to β-sheets, supporting the efficient formation of fibers consisting of hierarchically aligned silk nanofibrils. Both the as-sprayed fibers and the fibers washed with DI water to remove the PEG showed soft and stretchable properties. In some cases, however, the fibers were too soft, making them difficult to handle. This could be explained by at least three reasons: The first reason could be associated with the rapid conformational transition of silk fibroin from random coils to β-sheets when mixing silk solution of 5 minutes DT with PEG10k solution by pressing the spray pump. As a result, silk fibroin molecules may not have enough time to align along the fiber axis and organize hierarchically. The second reason could be attributed to Rayleigh instability, which explains the instability of electrospinning processes for fibers, and may force silk fibroin to be processed into undulated fiber structures with variations in diameter during spraying, resulting in poor mechanical properties. The third reason could be that the concentration of silk protein solution used in the present study, which is approximately 2% after mixing with PEG10k solution in the tube of the spray device, may not be sufficient to generate robust fibers, as natural silk spinning in silkworms and spiders generally utilizes an order of magnitude higher silk concentration in the spinning dope.

When the molecular weight of silk was decreased, i.e., the use of silk solutions of 30 minutes DT, the concentration of PEG10k, ionic strength, and pH played important roles in generating silk fibers, unlike the spraying using the silk solutions of 5 minutes DT. It was noted that the form of sprayed fibers prepared using the silk solution of 30 minutes DT was similar to those prepared using the silk solution of 5 minutes DT. In the case of spraying using the PEG10k dissolved in 1M sodium citrate buffer at pH=3, which is an environment of high ionic strength and low pH, microscale silk fibers with the formation of the local networks were produced at 4% PEG10k. Interestingly, the spider web-like fiber networks were produced when the concentration of PEG10k was increased to 8%. A further increase in the concentration of PEG10k to 16% resulted in well-defined macroscale silk fibers. When the high ionic strength was removed, i.e., the use of PEG10k dissolved in distilled water at pH=3 for spray, scattered microscale silk fibers without the formation of the networks were generated at 4% PEG10k. As the PEG10k concentration was increased, the scattered fibers began to interconnect at 8% PEG10k, and the formation of spider web-like fiber networks began to appear at 16% PEG10k. These results suggest that the concentration of PEG10k is an important factor for manipulating the morphology of fibers prepared at a low pH in the presence or absence of high ionic strength. In the case of spraying using the PEG10k dissolved in distilled water at pH=8, which is an environment of no ionic strength and high pH, no fiber formation was observed by optical microscopy. However, it should be noted that well-defined macroscale silk fibers were generated under the same conditions when silk solutions of 5 minutes DT were used for spray, unlike the use of silk solutions of 30 minutes DT. This result indicates that the key to the formation of silk fibers at high pH is the molecular weight, such that high molecular weight silk (i.e., silk solution of 5 minutes DT) may facilitate chain alignment that can result in a robust fiber matrix under shear and elongational flow when compared to the relatively lower molecular weight silk (i.e., silk solution of 30 minutes DT).

To investigate the applicability of sprayed fiber scaffolds as potential carriers for drug delivery, drug-loaded silk fibers and aerosols were fabricated in situ using the spray device, where rhodamine B was used as a model drug because it emits red fluorescence after excitation, allowing the loading of drug molecules in silk scaffolds to be easily tracked. The rhodamine B-loaded silk fibers or aerosols were generated upon spraying by controlling the molecular weight of silk, and collected on the Petri dishes, followed by washing with DI water to remove the PEG. Fluorescence images displayed that rhodamine B molecules emitting red fluorescence were well-distributed within the fibers and aerosols. This result could be attributed to the strong binding of rhodamine B to silk fibroin molecules through electrostatic and hydrophobic interactions arising from their positively charged and hydrophobic moieties, providing useful insight into loading of other drugs as extensively studied previously with silk carriers.

Figure 9:
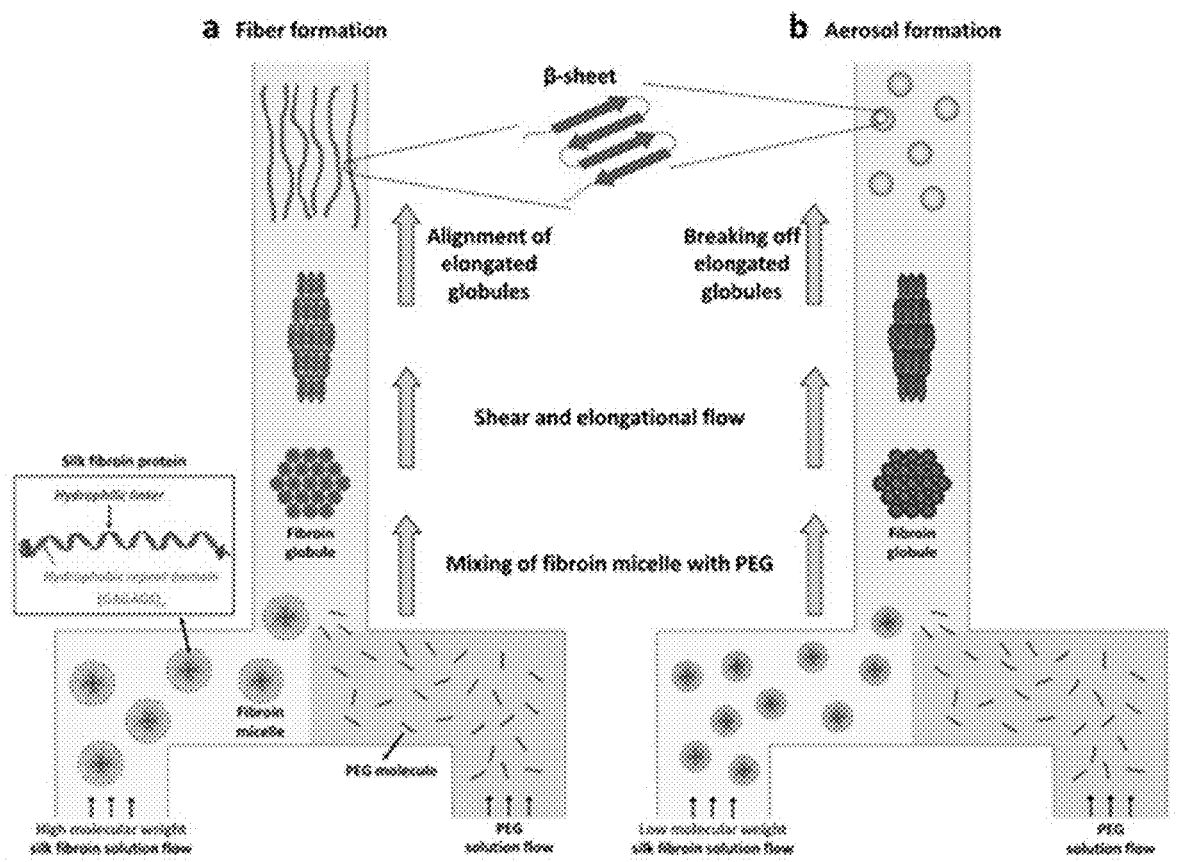
FIG. 9 is a schematic of a proposed mechanism of generating silk fibroin fibers and aerosols, in accordance with aspects of the present disclosure.

In general, shear and elongational flow play critical roles in the formation of natural silk fibers spun by silkworms and spiders. Upon spinning, the silk protein solution (i.e., spinning dope) stored in silk glands flows down an S-shaped tapered spinning duct and is subjected to shear and elongational flow along with pH gradient and metal ion exchange. Once sufficiently deformed, the silk protein goes through a stress-induced phase transition, dehydrating, and phase separating, eventually aggregating to form a robust fiber with enriched β-sheet conformation. FIG. 6 illustrates the proposed mechanism of fiber (FIG. 9, left) and aerosol (FIG. 9, right) generation in situ using the spray device by controlling the molecular weight of silk. Typically, silk fibroin consists of hydrophobic and hydrophilic segments. Although 73% of the amino acid residues are hydrophobic, there are still a significant number of amino acids with polar side moieties, such as glutamic acid, aspartic acid, serine, and tyrosine residues, that have a high affinity for water. PEG is a highly hydrophilic molecule and when mixed with silk solution in the mixing tube of the spray device, PEG molecules rapidly diffuse into the hydrophilic regions of silk fibroin micelles that form globules via intermicellar interactions. This allows water in the vicinity of silk fibroin to be removed by the PEG molecules, inducing the hydrophobic regions of silk fibroin to assemble and fold and resulting in immediate silk structural transition from random coils to β-sheets crystalline structures. In the meantime, the silk fibroin globules with PEG molecules are sheared and elongated, as they pass through the mixing tube. We hypothesize that higher molecular weight silk (i.e., silk solutions of 5 and 30 minutes DT) would aid the generation of a robust fiber matrix consisting of aligned silk nanofibril structures under the shear and elongational flow generated in the tube of the spray device due to the formation of stronger chain-chain interactions and the case of chain alignment, while preventing disconnecting and forming particles (FIG. 9, left). In the case of using the silk solutions of 30 minutes DT, the PEG concentration, ionic strength, and pH conditions can come into play as variables to manipulate the morphologies of the sprayed fibers. In contrast, when low molecular weight silk (i.e., silk solution of 180 minutes DT) was used, the sheared and elongated silk fibroin globules break off at the final stage of processing in the mixing tube owing to the weak intermicellar interactions, resulting in the formation of particles, instead of fibers, followed by directly spraying into air as aerosols (FIG. 9, right).

We demonstrated that silk aerosols or fibers can be fabricated in situ via immediate silk conformational transitions from random coils to β-sheet crystalline structures by mixing silk and PEG10k solutions using a spray device, where the molecular weight of silk was the key factor to determine fiber or aerosol formation. The use of the higher molecular weight silk, i.e., silk solutions of 5 and 30 minutes DT, resulted in fiber formation while avoiding the formation of particles due to break up during the shear and elongated fibroin globule stages in the mixing tube of the spray device. In contrast, the low molecular weight silk, i.e., silk solution of 180 minutes DT, caused the sheared and elongated fibroin globules to break up into particles due to the weak intermicellar interactions, leading to the generation of aerosols. We were also able to load a model drug into the sprayed fibers and aerosols. This work may have distinct benefits for the direct conformal deposition of silk protein-based materials onto target surfaces, including materials as coating, and tissues of the body, such as wound and burn sites.

Equivalents and Scope. The recitation of a listing of elements in any definition of a variable herein includes definitions of that variable as any single element or combinations (or sub-combinations) of listed elements. The recitation of an embodiment herein includes that embodiment as any single embodiment or in combination with any other embodiments or portions thereof. Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of making in situ silk fibroin aerosols and/or fibers, the method comprising:

rapidly mixing a silk fibroin solution and a beta sheet initiation solution under shear force to provide a mixed solution having rapidly initiated formation of beta sheet crystal structure, wherein the silk fibroin solution and the beta sheet initiation solution are prevented from contacting one another prior to the rapidly mixing, wherein the silk fibroin solution contains silk fibroin fragments having a molecular weight distribution, wherein the beta sheet initiation solution comprises a hygroscopic polymer having a molecular weight of between 7.5 kDa and 15.0 kDa; and rapidly expanding the mixed solution, thereby providing elongation force to the mixed solution and making the silk fibroin aerosols and/or fibers, wherein the rapidly mixing and the rapidly expanding steps occur within 1 second of one another, wherein the method makes the silk fibroin aerosols when the molecular weight distribution is below an aerosol-fiber threshold, wherein the method makes the silk fibroin fibers when the molecular weight distribution is above the aerosol-fiber threshold.

2. The method of claim 1, wherein the rapidly mixing under shear force is achieved by drawing a portion of the silk fibroin solution and a portion of the beta sheet initiation solution into a mixing chamber under shear force conditions.

3. The method of claim 2, wherein drawing the portion of the silk fibroin solution and the portion of the beta sheet initiation solution is achieved by pumping fluid out of the mixing chamber to produce a negative pressure therein to initiate the drawing.

4. The method of claim 3, wherein the pumping fluid is via a manual pump.

5. The method of claim 3, wherein the pumping fluid is via a non-manual pump.

6. The method of claim 1, wherein the rapidly mixing under shear force is achieved by pushing a portion of the silk fibroin solution and a portion of the beta sheet initiation solution into a mixing chamber under shear force conditions.

7. The method of claim 6, wherein the pushing the portion of the silk fibroin solution and the portion of the beta sheet initiation solution is achieved by elevating pressure within the silk fibroin solution and the beta sheet initiation solution to initiate the pushing.

8. The method of claim 7, wherein the elevating pressure is via a manual pump.

9. The method of claim 7, wherein the elevating pressure is via a non-manual pump.

10. The method of claim 1, wherein the method does not use compressed gas.

11. The method of claim 1, wherein the method does not use an applied electric field.

12. A spray device for making in situ silk fibroin aerosols and/or fibers, the spray device comprising a first reservoir, a second reservoir, a fluid pathway including a rapid shear mixing chamber and a rapid expansion chamber, and a pump, wherein the first reservoir contains a silk fibroin solution and the second reservoir contains a beta sheet initiation solution, wherein the silk fibroin solution contains fragments having a molecular weight distribution, wherein the beta sheet initiation solution comprises a hygroscopic polymer having a molecular weight of between 7.5 kDa and 15.0 kDa, wherein the pump is operatively coupled to the first reservoir, the second reservoir, the rapid shear mixing chamber, and the rapid expansion chamber, such that when the pump is activated, the spray device does the following:

rapidly mixes the silk fibroin solution and the beta sheet initiation solution under shear force to provide a mixed solution having rapidly initiated formation of beta sheet crystal structure; and rapidly expands the mixed solution, thereby providing elongation force to the mixed solution and making the silk fibroin aerosols and/or fibers, wherein the pump rapidly mixes and rapidly expands within 1 second of one another, wherein the spray device makes the silk fibroin aerosols when the molecular weight distribution is below an aerosol-fiber threshold, wherein the spray device makes the silk fibroin fibers when the molecular weight distribution is above the aerosol-fiber threshold.

13. The method of claim 1, wherein a concentration of the silk fibroin and a relative proportion of the silk fibroin solution and the beta sheet initiation solution in the rapidly mixing produces the mixed solution comprising the silk fibroin in an amount by weight of at least 0.5% and at most 30.0%.

14. The method of claim 1, wherein a concentration of the hygroscopic polymer in the beta sheet initiation solution and a relative proportion of the silk fibroin solution and the beta sheet initiation solution in the rapidly mixing produces the mixed solution comprising the hygroscopic polymer in an amount by weight of at least 0.5% and at most 30.0%.

15. The method of claim 1, wherein the rapidly mixing involves a ratio by volume of silk fibroin solution to beta sheet initiation solution of at least 4:1 and at most 1:4.

16. The method of claim 1, wherein the rapidly mixing involves equal parts by volume of silk fibroin solution and beta sheet initiation solution.

17. The method of claim 1, wherein the silk fibroin aerosols have a diameter of between 0.1 μm and 25 μm.

18. The method of claim 1, wherein the silk fibroin fibers have a length of at least 1 cm.

19. A kit comprising a first reservoir containing a silk fibroin solution, a second reservoir containing a beta sheet initiation solution, wherein the kit maintains physical separation of the silk fibroin solution and the beta sheet initiation solution, wherein the first reservoir and the second reservoir are accessible to allow their contents to be removed and rapidly mixed, wherein the silk fibroin solution has fragments a molecular weight distribution that is above or below an aerosol-fiber threshold.

20. The method of claim 1, wherein the hygroscopic polymer is polyethylene glycol, polyethylene oxide, polyvinyl alcohol, or a combination thereof.

21. The method of claim 1, wherein the hygroscopic polymer is polyethylene glycol.

22. The method of claim 1, wherein the molecular weight distribution is above the aerosol-fiber threshold.

23. The method of claim 1, wherein the molecular weight distribution is below the aerosol-fiber threshold.

24. The method of claim 1, wherein the silk fibroin solution and/or the beta sheet initiation solution further include an active agent.

25. The method of claim 1, wherein the silk fibroin solution and/or the beta sheet initiation solution are free of organic solvents, including methanol.

\* \* \* \* \*

SEQUENCE LISTING

```
Sequence total quantity: 22
SEQ ID NO: 1               moltype = AA  length = 90
FEATURE                    Location/Qualifiers
REGION                     1..90
                           note = Synthetic polypeptide
VARIANT                    7..90
                           note = Wherein any of residues 7-90 may be missing.
source                     1..90
                           mol_type = protein
                           organism = synthetic construct
SEQUENCE: 1
GAGAGSGAGA GSGAGAGSGA GAGSGAGAGS GAGAGSGAGA GSGAGAGSGA GAGSGAGAGS  60
GAGAGSGAGA GSGAGAGSGA GAGSGAGAGS                                   90

SEQ ID NO: 2               moltype = AA  length = 30
FEATURE                    Location/Qualifiers
REGION                     1..30
                           note = Synthetic polypeptide
VARIANT                    2
```

```
                        note = Wherein X is V, I or A
VARIANT                 3..30
                        note = Wherein any of residues 3-30 may be missing
VARIANT                 4
                        note = Wherein X is V, I or A
VARIANT                 6
                        note = Wherein X is V, I or A
VARIANT                 8
                        note = Wherein X is V, I or A
VARIANT                 10
                        note = Wherein X is V, I or A
VARIANT                 12
                        note = wherein X=V, I, or A
VARIANT                 14
                        note = Wherein X is V, I or A
VARIANT                 16
                        note = Wherein X is V, I or A
VARIANT                 18
                        note = Wherein X is V, I or A
VARIANT                 20
                        note = Wherein X is V, I or A
VARIANT                 22
                        note = Wherein X is V, I or A
VARIANT                 24
                        note = Wherein X is V, I or A
VARIANT                 26
                        note = Wherein X is V, I or A
VARIANT                 28
                        note = Wherein X is V, I or A
VARIANT                 30
                        note = Wherein X is V, I or A
source                  1..30
                        mol_type = protein
                        organism = synthetic construct
SEQUENCE: 2
GXGXGXGXGX GXGXGXGXGX GXGXGXGXGX                                     30

SEQ ID NO: 3            moltype = AA  length = 4
FEATURE                 Location/Qualifiers
source                  1..4
                        mol_type = protein
                        organism = Bombyx mori
SEQUENCE: 3
GAAS                                                                 4

SEQ ID NO: 4            moltype = AA  length = 15
FEATURE                 Location/Qualifiers
REGION                  1..15
                        note = Synthetic polypeptide
VARIANT                 2
                        note = Wherein residue S may be missing
VARIANT                 14..15
                        note = Wherein any of residues 14-15 may be missing
source                  1..15
                        mol_type = protein
                        organism = synthetic construct
SEQUENCE: 4
SSAAAAAAAA AAAAA                                                     15

SEQ ID NO: 5           moltype =   length =
SEQUENCE: 5
000

SEQ ID NO: 6           moltype =   length =
SEQUENCE: 6
000

SEQ ID NO: 7           moltype = AA  length = 12
FEATURE                 Location/Qualifiers
REGION                  1..12
                        note = Synthetic polypeptide
VARIANT                 2
                        note = Wherein residue S may be missing
VARIANT                 4..6
                        note = Wherein any residues 4-6 may be missing
source                  1..12
                        mol_type = protein
                        organism = synthetic construct
```

-continued

```
SEQUENCE: 7
SSAAAASSAA AA                                                              12

SEQ ID NO: 8            moltype = AA   length = 6
FEATURE                Location/Qualifiers
source                 1..6
                       mol_type = protein
                       organism = Galleria mellonella
SEQUENCE: 8
GLGGLG                                                                      6

SEQ ID NO: 9            moltype = AA   length = 6
FEATURE                Location/Qualifiers
REGION                 1..6
                       note = Synthetic polypeptide
VARIANT                2
                       note = Wherein X is L, I, V or P
VARIANT                5
                       note = Wherein X is L, I, V or P
source                 1..6
                       mol_type = protein
                       organism = synthetic construct
SEQUENCE: 9
GXGGXG                                                                      6

SEQ ID NO: 10           moltype = AA   length = 21
FEATURE                Location/Qualifiers
REGION                 1..21
                       note = Synthetic polypeptide
VARIANT                5
                       note = Wherein X is Y, V, S or A
VARIANT                6..20
                       note = Wherein any of 6-20 may be missing
VARIANT                10
                       note = Wherein X is Y, V, S or A
VARIANT                15
                       note = Wherein X is Y, V, S or A
VARIANT                20
                       note = Wherein X is Y, V, S or A
source                 1..21
                       mol_type = protein
                       organism = synthetic construct
SEQUENCE: 10
GPGGXGPGGX GPGGXGPGGX Y                                                     21

SEQ ID NO: 11           moltype = AA   length = 5
FEATURE                Location/Qualifiers
source                 1..5
                       mol_type = protein
                       organism = Argiope trifasciata
SEQUENCE: 11
GRGGA                                                                       5

SEQ ID NO: 12           moltype = AA   length = 13
FEATURE                Location/Qualifiers
REGION                 1..13
                       note = Synthetic polypeptide
VARIANT                5..10
                       note = Wherein any of 5-10 may be missing
source                 1..13
                       mol_type = protein
                       organism = synthetic construct
SEQUENCE: 12
GAGAAAAAAA GGA                                                              13

SEQ ID NO: 13           moltype = AA   length = 8
FEATURE                Location/Qualifiers
REGION                 1..8
                       note = Synthetic polypeptide
VARIANT                3
                       note = Wherein X is Q, Y, L, A, S or R
VARIANT                5
                       note = Wherein X is Q, Y, L, A, S or R
VARIANT                7
                       note = Wherein X is Q, Y, L, A, S or R
VARIANT                8
                       note = Wherein X is Q, Y, L, A, S or R
```

-continued

```
source                      1..8
                            mol_type = protein
                            organism = synthetic construct
SEQUENCE: 13
GGXGXGXX                                                                    8

SEQ ID NO: 14               moltype = AA  length = 16
FEATURE                     Location/Qualifiers
source                      1..16
                            mol_type = protein
                            organism = Bombyx mori
SEQUENCE: 14
TGSSGFGPYV NGGYSG                                                           16

SEQ ID NO: 15               moltype = AA  length = 8
FEATURE                     Location/Qualifiers
source                      1..8
                            mol_type = protein
                            organism = Bombyx mandarina
SEQUENCE: 15
YEYAWSSE                                                                    8

SEQ ID NO: 16               moltype = AA  length = 7
FEATURE                     Location/Qualifiers
source                      1..7
                            mol_type = protein
                            organism = Antheraea mylitta
SEQUENCE: 16
SDFGTGS                                                                     7

SEQ ID NO: 17               moltype = AA  length = 7
FEATURE                     Location/Qualifiers
source                      1..7
                            mol_type = protein
                            organism = Antheraea yamamai
SEQUENCE: 17
RRAGYDR                                                                     7

SEQ ID NO: 18               moltype = AA  length = 8
FEATURE                     Location/Qualifiers
source                      1..8
                            mol_type = protein
                            organism = Galleria mellonella
SEQUENCE: 18
EVIVIDDR                                                                    8

SEQ ID NO: 19               moltype = AA  length = 18
FEATURE                     Location/Qualifiers
source                      1..18
                            mol_type = protein
                            organism = Nephila madascariensis
SEQUENCE: 19
TTIIEDLDIT IDGADGPI                                                         18

SEQ ID NO: 20               moltype = AA  length = 8
FEATURE                     Location/Qualifiers
source                      1..8
                            mol_type = protein
                            organism = Nephila clavipes
SEQUENCE: 20
TISEELTI                                                                    8

SEQ ID NO: 21               moltype = AA  length = 6
FEATURE                     Location/Qualifiers
REGION                      1..6
                            note = Synthetic polypeptide
source                      1..6
                            mol_type = protein
                            organism = synthetic construct
SEQUENCE: 21
GSGAGA                                                                      6

SEQ ID NO: 22               moltype =   length =
SEQUENCE: 22
000
```